United States Patent
Welles et al.

(10) Patent No.: US 11,585,797 B2
(45) Date of Patent: Feb. 21, 2023

(54) DYNAMIC AND REAL-TIME CORRECTION OF DIFFERENTIAL MEASUREMENT OFFSETS IN A GAS ANALYSIS SYSTEM

(71) Applicant: Li-Cor, Inc., Lincoln, NE (US)

(72) Inventors: Jon Welles, Lincoln, NE (US); Aaron Saathoff, Lincoln, NE (US)

(73) Assignee: Li-Cor, Inc., Lincoln, NE (US)

(*) Notice: Subject to any disclaimer, the term of this patent is extended or adjusted under 35 U.S.C. 154(b) by 362 days.

(21) Appl. No.: 16/905,230

(22) Filed: Jun. 18, 2020

(65) Prior Publication Data
US 2020/0408729 A1  Dec. 31, 2020

Related U.S. Application Data

(60) Provisional application No. 62/868,181, filed on Jun. 28, 2019.

(51) Int. Cl.
*G01N 33/00* (2006.01)

(52) U.S. Cl.
CPC ....... *G01N 33/0031* (2013.01); *G01N 33/004* (2013.01); *G01N 33/0098* (2013.01)

(58) Field of Classification Search
CPC ............. G01N 33/0031; G01N 33/004; G01N 33/0098
See application file for complete search history.

(56) References Cited

U.S. PATENT DOCUMENTS

2008/0281193 A1  11/2008  Ben Oren et al.
2010/0262382 A1* 10/2010  Lighton ............. G01N 33/0067
                                                    702/45

(Continued)

FOREIGN PATENT DOCUMENTS

KR  10/1982/0000744 B1  5/1982
KR  10/2008/0036633 A   4/2008

OTHER PUBLICATIONS

Written Opinion of the International Search Authority, dated Oct. 6, 2020 in Application No. PCT/US2020/039097.

(Continued)

*Primary Examiner* — Daniel S Larkin
*Assistant Examiner* — Fatemeh Esfandiari Nia
(74) *Attorney, Agent, or Firm* — Gerald T. Gray; Leydig, Voit & Mayer, Ltd.

(57) ABSTRACT

Systems and method for automatically determining offset correction values in a differential measurement system, and for correcting measurement offsets between two measurement devices in the differential measurement system. A method for determining real-time offset corrections in a gas analysis system having first and second gas analyzers includes for each of a plurality of gas concentrations within a range of gas concentrations: a) supplying the concentration of gas to the first and second gas analyzers through first and second gas flow lines, respectively; b) measuring a first gas concentration value using the first gas analyzer; and c) measuring a second gas concentration value using the second gas analyzer. The method may also include determining an offset value between each corresponding first and second gas concentration value, and determining a functional relationship between the offset values and gas concentration measurements of the first gas analyzer.

21 Claims, 3 Drawing Sheets

(56) References Cited

U.S. PATENT DOCUMENTS

| | | | |
|---|---|---|---|
| 2012/0181432 A1* | 7/2012 | Welles | G01N 21/274 |
| | | | 250/340 |
| 2013/0165806 A1* | 6/2013 | Wondka | A61B 5/0816 |
| | | | 600/532 |
| 2015/0253297 A1* | 9/2015 | Ning | G01J 3/42 |
| | | | 250/341.1 |
| 2015/0369784 A1* | 12/2015 | Friedrich | G01N 33/0032 |
| | | | 436/143 |
| 2018/0136184 A1 | 5/2018 | Morgan et al. | |
| 2018/0321207 A1 | 11/2018 | Hellgren et al. | |

OTHER PUBLICATIONS

International Search Report of the International Search Authority, dated Oct. 6, 2020 in Application No. PCT/US2020/039097.

* cited by examiner

FIG. 1 (The line represents the linear least squares fit of a 3rd order polynomial to the match offset data)

ated by artifacts caused by factors such as temperature gradients, slight calibration differences between the two analyzers, and zero drift; these artifacts directly add error to the computed mole fraction difference that underlies the estimation of plant parameters A, E, and others.

DYNAMIC AND REAL-TIME CORRECTION OF DIFFERENTIAL MEASUREMENT OFFSETS IN A GAS ANALYSIS SYSTEM

CROSS-REFERENCE TO RELATED APPLICATIONS

This application claims the benefit of priority to U.S. Provisional Patent Application No. 62/868,181, filed Jun. 28, 2019, which is hereby incorporated by reference in its entirety.

BACKGROUND

Systems for measuring plant photosynthesis and transpiration rates can be categorized as open or closed systems. For open systems, the leaf or plant is enclosed in a sample chamber, and an air stream is passed continuously through the chamber. $CO_2$ and $H_2O$ concentrations of chamber influent and effluent are measured, and the difference between influent and effluent concentration is calculated. (Throughout this document the term "concentration" refers to mole fraction of a gas in natural or synthetic moist air, or mole fraction in natural or synthetic dry air ("dry mole fraction") where such is specified.) This difference may be used, along with the mass flow rate, to calculate photosynthesis ($CO_2$) and transpiration ($H_2O$) rates. For closed systems, the leaf or plant is enclosed in a chamber that is not supplied with fresh air. The concentrations of $CO_2$ and $H_2O$ are continuously monitored within the chamber. The rate of change of this concentration, along with the chamber volume, may be used to calculate photosynthesis ($CO_2$) and transpiration ($H_2O$) rates.

In many photosynthesis systems, a conditioned air stream is typically split into two streams. The first flow path (known as reference) passes through a gas analyzer (e.g., Infra-Red Gas Analyzer or IRGA), which measures constituent gas concentrations ($CO_2$ and $H_2O$). The second flow path (known as sample) passes through a sample chamber (leaf chamber) in which gas exchange occurs. This second sample flow path exits the chamber and enters a second gas analyzer (e.g., IRGA) or alternates with the reference air stream through a single gas analyzer. The differences between the sample and reference gas concentrations are used in calculating photosynthesis ($CO_2$) and transpiration ($H_2O$). As photosynthesis and transpiration measurements are based on concentration differences in these two gas streams, the accuracy in measuring the difference is more critical than measuring the absolute concentration of either. Persistent diffusive sources and/or sinks present in the tubing, connectors, and fittings that supply the head with the sample and reference gas streams can compromise measurement accuracy.

In the practice of taking gas-exchange measurements with gas analyzer instruments such as the LI-6400XT and LI-6800 (both produced and sold by LI-COR Biosciences), it becomes necessary to periodically match the gas analyzers (GAs), e.g., infra-red gas analyzers (IRGAs). The matching process is necessary because the basic principle underlying gas-exchange measurements relies on accurately computing the difference in gas mole fraction that is measured by two analyzers, termed the sample and reference analyzers. This difference is central to accurately estimating plant parameters such as $CO_2$ assimilation (A) and H2O transpiration (E). However, the difference in calculated gas mole fractions between the sample and reference analyzers can be contaminated by artifacts caused by factors such as temperature gradients, slight calibration differences between the two analyzers, and zero drift; these artifacts directly add error to the computed mole fraction difference that underlies the estimation of plant parameters A, E, and others.

A matching procedure has long been used to minimize the effects of artifacts in the computed differential between the sample and reference analyzers. During the matching procedure, changes may be made to the instrument flow path using an automated valve that forces both the sample and reference analyzers to see the same air at approximately the same time. Under such conditions, the analyzers should show identical $CO_2$ and $H_2O$ mole fractions. If they do not, the sample analyzer is forced to show an identical reading to the reference analyzer by adding an adjustment term to the computed gas mole fraction. The matching procedure takes approximately 30 seconds during which time normal measurements become impossible because of the flow path changes. Additionally, the matching procedure needs to be conducted when certain thresholds are met such as in time passage, gas mole fraction change, temperature change, or when small fluxes are being measured. Every time the IRGA matching procedure is used, normal measurements are not possible, and after the matching procedure ends, a certain amount of time (e.g., 15-30 seconds) is required for IRGA washout to occur and instrument control loops to become re-established. In certain applications, such as measuring $CO_2$ response curves, the matching procedure needs to be conducted at nearly every step, which can add running time to the overall experiment.

SUMMARY

The present disclosure provides systems and method for automatically determining offset correction values in a differential measurement system, and for correcting measurement offsets between two measurement devices in the differential measurement system.

According to an embodiment, a method is provided for determining real-time offset corrections in a gas analysis system having a first gas analyzer and a second gas analyzer, the method comprising, for each of a plurality of gas concentrations within a range of gas concentrations: a) supplying the concentration of gas to the first gas analyzer through a first gas flow line and to the second gas analyzer through a second gas flow line; b) measuring a first gas concentration value using the first gas analyzer; and c) measuring a second gas concentration value using the second gas analyzer. The method may also include determining an offset value between each corresponding first and second gas concentration value, and determining a functional relationship between the offset values and gas concentration measurements of the first gas analyzer.

In certain aspects, the supplying includes varying the concentration of the gas from a first concentration to a second concentration, and during the varying, the measuring a first gas concentration value using the first gas analyzer includes measuring, at each of a first plurality of measurement times, a first concentration of the gas using the first gas analyzer, and the measuring a second gas concentration value using the second gas analyzer includes simultaneously measuring, at each of the first plurality of measurement times, a second concentration of the gas using the second gas analyzer. In certain aspects, the measuring of the first and second gas concentration values occurs when the concentration of gas supplied to the first gas analyzer and to the second gas analyzer reaches a steady state.

In certain aspects, the determining a functional relationship includes applying a fit function to the offset values. In certain aspects, the fit function includes a least squares fit. In certain aspects, the determining a functional relationship includes segmenting the offset values into two or more range segments, each range segment corresponding to a portion of the range of gas concentrations, and for each range segment applying a separate segment fit function to the offset values in that range segment.

In certain aspects, the method may further include taking real-time gas measurements and adjusting measurement values of the first gas analyzer based on the functional relationship. In certain aspects, the gas analysis system further includes an enclosed sample chamber defining a measurement volume for analysis of a photosynthesis capable sample, the sample chamber having an inlet port coupled with the first gas flow line and an outlet port coupled with an inlet port of the first gas analyzer, and the method further includes, with a photosynthesis capable sample in the sample chamber, taking real-time gas measurements using a gas concentration within the specified concentration range and adjusting gas concentration measurement values of the first gas analyzer based on the determined functional relationship. In certain aspects, the photosynthesis capable sample includes a leaf.

In certain aspects, the gas includes $CO_2$, and the varying the concentration of $CO_2$ includes only increasing the concentration of $CO_2$, or only decreasing the concentration of $CO_2$, or varying the concentration of $CO_2$ from a first value to a second value and then varying the concentration of $CO_2$ from the second value to the first value.

In certain aspects, the measuring of the first and second gas concentration values occurs when the concentration of gas supplied to the first gas analyzer and to the second gas analyzer reaches a steady state.

According to another embodiment, a gas analysis system, such as a gas exchange analysis system is provided for implementing the methods described herein. For example, according to an embodiment, a gas analysis system is provided that includes a gas source coupled to a first gas flow line and a second gas flow line, a first gas analyzer coupled to a first gas flow line and configured to measure a first concentration of the gas received from the first gas flow line, a second gas analyzer coupled to a second gas flow line and configured to measure a second concentration of the gas received from the second gas flow line, and a control circuit. In some embodiments, the control circuit is configured to send a control signal to the gas source to control the gas source to adjust a concentration of a gas provided to the first and second gas flow lines for each of a plurality of gas concentrations within a range of gas concentrations; and for each of the plurality of gas concentration values: receive a first gas concentration measurement value from the first gas analyzer; and receive a second gas concentration measurement value from the second gas analyzer. In some embodiments, the control circuit is further configured to determine an offset value between each corresponding first and second gas concentration value, and to determine a functional relationship between the offset values and gas concentration measurements of the first gas analyzer.

According to an embodiment, a method is provided for determining real-time offset corrections in a differential measurement system having a first measurement device and a second measurement device. The method includes for each of a plurality of property values of a physical property within a range of property values: a) obtaining a first measurement value of the physical property using the first measurement device; and b) obtaining a second measurement value of the physical property using the second measurement device. The method may also include determining an offset value between each corresponding first and second measurement value; and determining a functional relationship between the offset values and property measurements of the first measurement device.

In certain aspects, the method further includes taking real-time property measurements and adjusting measurement values of the first measurement device based on the functional relationship or adjusting measurement values of the second measurement device based on the functional relationship or adjusting a difference between measurement values of the first measurement device and the second measurement device based on the functional relationship.

In certain aspects, each of the first and second measurement devices includes one of a gas analyzer, or a humidity sensor, or a pressure sensor, or a temperature sensor, or a light or radiation sensor, and the physical property includes a gas concentration, or humidity, or pressure, or temperature, or a light wavelength or intensity, respectively.

According to another embodiment, a differential measurement system, such as a gas exchange analysis system is provided for implementing the methods described herein. For example, according to an embodiment, a differential measurement system is provided that includes a first measurement device configured to measure a physical property, a second measurement device configured to measure the physical property, and a control circuit including for example a processor and associate memory storing code for executing aspects of the methods. In some embodiments, the control circuit is configured to, for each of a plurality of property values of the physical property within a range of property values, receive a first measurement value of the physical property from the first measurement device, and receive a second measurement value of the physical property from the second measurement device. In some embodiments, the control circuit is further configured to determine an offset value between each corresponding first and second measurement value, and determine a functional relationship between the offset values and measurements of the first measurement device.

In certain aspects, the control circuit is further configured to control the system to take real-time property measurements and adjust measurement values of the first measurement device based on the functional relationship.

In certain aspects, each of the first and second measurement devices includes one of a gas analyzer, or a humidity sensor, or a pressure sensor, or a temperature sensor, or a light or radiation sensor, and the physical property includes a gas concentration, or humidity, or pressure, or temperature, or a light wavelength or intensity, respectively.

In a further embodiment, a non-transitory computer readable medium is provided that stores instructions, which when executed by one or more processors, cause the one or more processors to implement a method of automatically determining real-time offset corrections in a differential measurement system as described herein.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWINGS

The detailed description is described with reference to the accompanying figures. The use of the same reference numbers in different instances in the description and the figures may indicate similar or identical items.

DETAILED DESCRIPTION

Figure 1:
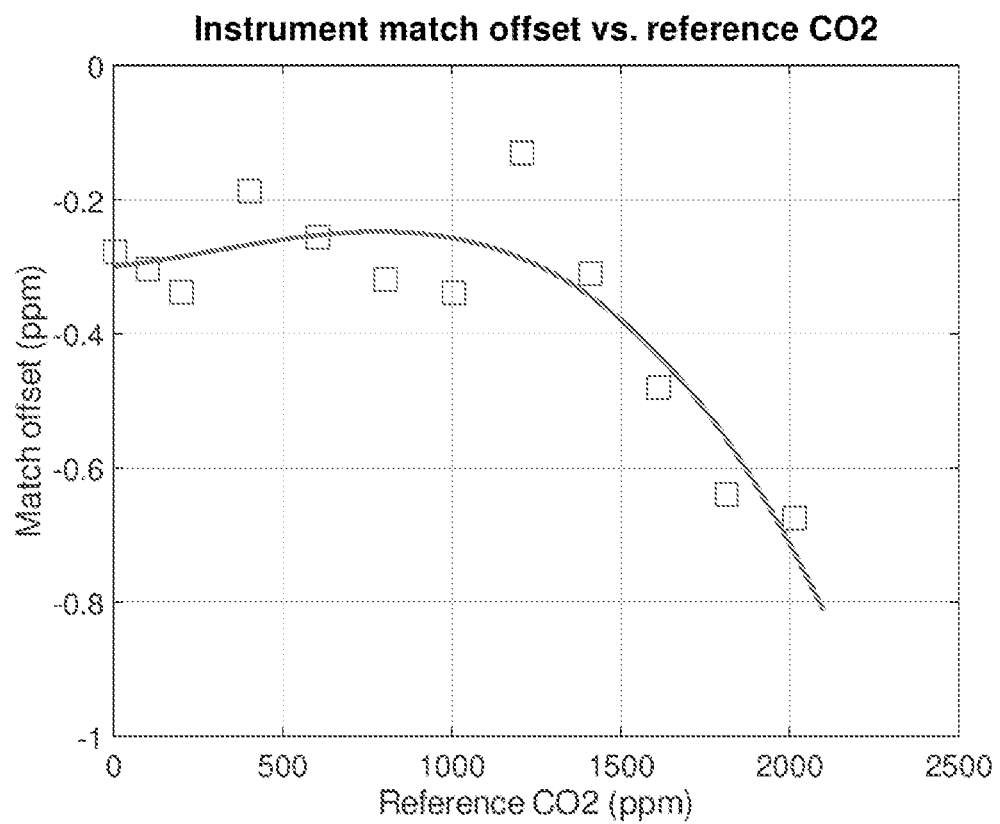
FIG. 1 illustrates an example of instrument match offset data plotted v. $CO_2$ concentration according to an embodiment.

The present disclosure provides systems and method for automatically determining offset correction values in a differential measurement system, and for correcting measurement offsets between two measurement devices in the differential measurement system. One example of a differential measurement system is a gas analysis system, such as a gas exchange measurement system as may be used for measuring plant leaf gas exchange based upon instantaneous mass balance in a leaf chamber of the gas exchange measurement system. The techniques of the present disclosure are applicable to any differential measurement system wherein two (or more) measurement devices, e.g., sensors, measure the same physical property and determine a quantity of interest based on a difference between two (or more) absolute measurements.

The embodiments disclosed herein provide novel matching techniques based on characterizing the match space of the measurement devices. For a gas exchange measurement system, the match space of the gas analyzers, e.g., IRGAs, is characterized prior to taking any measurements with a plant in the chamber. During this new matching technique, differing $CO_2$ and/or $H_2O$ mole fractions may be run through the IRGAs, which allows for a more complete characterization of the IRGA match space than with the traditional single-point characterization that is currently implemented. From the data, a functional relationship between the reference gas analyzer and the match offset is developed. The functional relationship can then be used for real-time correction of the sample analyzer values. Use of the present embodiments advantageously avoids the need to match the IRGAs when gas mole fraction changes. Thus, current applications such as determining $CO_2$ response curves can be conducted without running an IRGA match routine at each step of the curve determination process. Furthermore, the present embodiments are useful for obtaining match-corrected data for non steady-state measurement techniques. Such non steady state techniques include determining a rapid net assimilation rate (Anet) to computed sample internal $CO_2$ concentration (Ci) response (RACiR) curve for a photosynthesis capable sample.

Embodiments rely upon characterizing the match space between the sensors, e.g., IRGAs, in response to a varying input and developing a functional relationship between that varying input and the resultant match offset. For example, in an embodiment, a match offset function is determined as follows: Match offset=f(x), where x is the input that is being varied and f(x) is the functional relationship between that varying input and the resulting match offset. In contrast, in a current gas analysis system implementation, a gas analyzer matching function may be: Match offset=y, where y is a constant and unchanging value calculated from the gas analyzer matching routine. When system inputs change sufficiently, this value (y) is no longer representative of the match offset and needs to be re-calculated by running the gas analyzer match routine again. With the functional relationship from the present embodiment, this is no longer required.

It should be appreciated that any input that affects the matching behavior between two sensors or analyzers can be developed into a functional form, provided that the input can be varied and a sufficient number of variations can be achieved so that the sensor/analyzer matching response can be characterized by a sufficient number of data points that allows for a robust functional characterization of the sensor/analyzer match response. Furthermore, the present embodiments apply to any measurement based on a difference between measurements of the same physical property by two sensors/analyzers. In gas analysis systems, focus may be on changes in gas mole fraction as the input, but gas analyzer (e.g., IRGA) match response to other inputs that affect matching behavior (such as flow rate or temperature) may be characterized as well.

Certain method embodiments will now be discussed in the context of a gas exchange analysis system. In a first embodiment (method 1), the instrument's $CO_2$ or $H_2O$ control system is set to target a series of $CO_2$ or $H_2O$ mole fractions. Once the gas mole fraction is stable in the reference and sample analyzers, data is logged and the control system moves on to the next set point. This process continues until the desired concentration range is covered, for example about 10-20 discreet data points. After this, the data can be post-processed to calculate the gas analyzer match offset at each control system set point, and a functional relationship between the match offset and reference gas analyzer can be developed. This functional relationship then serves as the basis for calculating the gas analyzer offset correction in real time based on the reference analyzer mole fraction during real-time gas measurements.

In a second embodiment (method 2), the $CO_2$ or $H_2O$ mole fraction is ramped, e.g., from one mole fraction to a second mole fraction. The ramping may be linear or non-linear. For example, the $CO_2$ control system could linearly ramp $CO_2$ from 5 to 2000 ppm over a given period of time. In some embodiments, the ramping includes continuously varying the gas concentration over the desired range. In some embodiments, the ramping includes step-wise changes in the gas concentration over the desired range. During this ramping period, data is periodically or continuously recorded, and from this data the gas analyzer match offset is calculated. Again, a functional relationship is developed between the reference analyzer mole fraction and the match offset, and this relationship is used for real-time match offset adjustments or corrections during real-time measurements. The adjustments or corrections may be made to the measured values of either sensor/analyzer or to the determined difference in values between the sensors/analyzers.

In method 2, some additional complicating factors may be present that do not occur in method 1. One factor is that during the ramping period, the residence time distribution (RTD) characteristics for the analyzers should be identical or very nearly identical in time in order for reliable match offset data to be collected. If the RTDs are not identical in time, the apparent match offset will be biased and the functional representation of the gas analyzer match offset may be incorrect. The underlying reason for the differing RTDs are the different flow paths of the sample and reference gas analyzers and the resulting differences in the effective volumes of the sample and reference gas analyzers which governs the fundamental mean residence time and dynamic response characteristics of each gas analyzer. In some instruments, such as in the LI-6800, built-in flow sensors and valves may be used to configure the instrument such that the RTDs are equal in time (or very close to equal) between the sample and reference gas analyzers, and thus the ramping approach (method 2) is able to yield reliable match offset data. The equality of the sample and reference analyzer RTDs can be assessed by ramping $CO_2$ up and then down (or down and then up) in concentration; if the RTDs are equal the calculated match offset values will overlap and will not be dependent on the direction of the ramping.

Accordingly, in certain embodiments, the ramping or varying of the concentration of the gas, e.g., $CO_2$, includes only increasing the concentration of the gas, or only decreasing the concentration of the gas, or varying the concentration of the gas from a first value to a second value and then varying the concentration of the gas from the second value to the first value. In other measurement systems, the ramping or varying of the physical property being measured, e.g., humidity, temperature, pressure, light wavelength, light intensity, etc, includes only increasing the physical property, or only decreasing the physical property, or varying the physical property from a first value to a second value and then varying the physical property from the second value to the first value.

In certain embodiments, the functional relationship may be established by applying a fit function to the collected data, e.g., using a linear least squares fitting approach to the match offset versus the varied input (x). The varied input (x) serves as the independent variable and the match offset is the dependent variable for the fit. For example, match offset versus reference analyzer $CO_2$ mole fraction can be fit using a line or a polynomial, depending upon which may produce a better fit. FIG. 1 illustrates an example of instrument match offset data plotted v. $CO_2$ concentration as acquired using method 1. The line shown represents a linear least squares fit of a 3rd order polynomial to the match offset data.

Additionally, for embodiments utilizing a ramping input, such as ramping $CO_2$, the fitting domain can be sub-divided into regions and each region can be fit with a function that more precisely captures the match offset behavior over that limited region. For example, a $CO_2$ matching data set may have match offset data over $CO_2$ mole fractions between 5 and 2000 ppm. These mole fractions can be sub-divided into regions, for example 5-400, 401-800, 801-1200, 1201-1600, 1601-2000 ppm; each region is then fit with its own function, and the instrument can then use the appropriate function for real-time offset correction depending upon what $CO_2$ concentration is currently being used. In certain embodiments, 3rd order polynomials may produce good fitting results, and fitting small $CO_2$ concentration ranges (e.g., 5-400 ppm) may reduce overall error. Once the data has been fit and the coefficients of the function have been calculated, the function can then be implemented and used in real-time offset correction of the sample analyzer.

In another embodiment, a look-up table and/or a regional averaging of the match offsets over a given property value (e.g., concentration) range may be used.

Benefits of the present embodiments in the context of gas analysis systems include a reduction or even elimination of the need for stopping measurements to match the gas analyzers, particularly during $CO_2$ response curve measurements which require frequent analyzer matching. Furthermore, the embodiments are advantageous for the development of non steady-state techniques, such as RACiR techniques which use a continuously changing $CO_2$ input to rapidly assess the $CO_2$ response characteristics of a plant. For RACiR techniques, and other non-steady state measurements, real-time offset correction of the sample analyzer is needed for the technique to be successfully implemented. U.S. Patent Application Publication No. 2018/0136184 A1 (corresponding to U.S. application Ser. No. 15/811,210), discusses various aspects of RACiR techniques and is incorporated herein by reference for all purposes.

Figure 3:
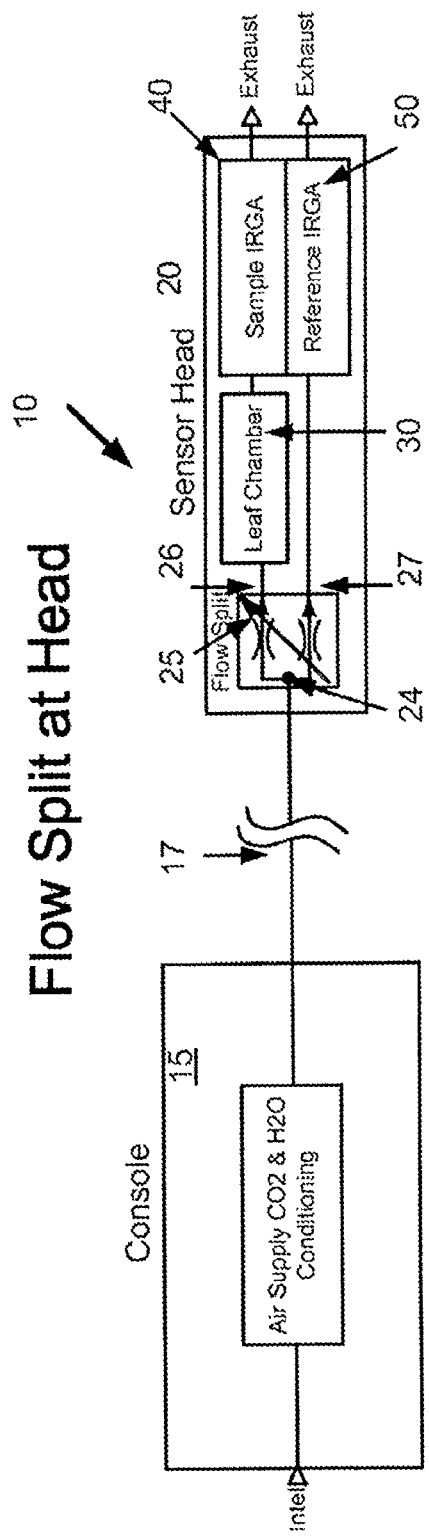
FIG. 3 illustrates an example of a gas exchange measurement system 10 according to one embodiment.

FIG. 3 illustrates an example of a gas exchange measurement system 10 according to one embodiment. Gas exchange measurement system 10 in one embodiment includes a console 15 and a sensor head 20 remote from console 15. Other system embodiments may include an integrated console and sensor head or sensor module. Console 15 typically includes, or is connected with, one or more gas sources and gas conditioning equipment. For example, in the context of photosynthesis and transpiration measurements, gas sources could include reservoirs of $CO_2$ and $H_2O$, and conditioning equipment for controlling and conditioning each gas concentration in a gas flow line. A flow path or gas flow line 17 connecting console 15 with sensor head 20 typically includes flexible tubing and connectors. Flow path 17 provides a single stream or gas flow path to flow splitting device or mechanism 25 in sensor head 20. Flow splitting device or mechanism 25 receives a stream of gas from console 15 and splits the flow into two separate flow paths as will be described in more detail below. Flow splitting device or mechanism 25 acts as a source of gas; one stream is provided to the chamber 30 (e.g., sample stream) and the other stream (e.g., reference stream) is provided to a reference gas analyzer 50. A second gas analyzer 40 receives and analyzes gas exiting from chamber 30. Reference gas analyzer 50 and second gas analyzer 40 might each include an Infra-Red Gas Analyzer (IRGA), as is known in the art, or other gas analyzer. In some embodiments, valves and conduits allow for routing the gas flow around chamber 30 to second gas analyzer 40, hence removing chamber 30 from the flow line between the source and the second gas analyzer 40.

It is desirable that flow path lengths and the number of connections downstream of the flow split device or mechanism 25 location be minimized to reduce parasitic sources and sinks which may differentially affect concentrations in the two flow paths, e.g., to further minimize any parasitic sources and sinks which impact the sample and reference streams independently are advantageously minimized.

In an embodiment, a control system (not shown), e.g., including one or more processors and associated memory, may control various system components to control the flow of gas in system 10. For example, the control system may control the amount or concentration of gas provided from the console 15 and may control flow rates provided to the gas analyzers 40, 50 by flow split device or mechanism 25, and may control the configuration of flow paths, e.g., bypassing sample chamber 30. In an embodiment, the control system controls the concentration of gas provided to the gas analyzers 40, 50, e.g., for match offset determination. For example, in an embodiment, the control system may control the $CO_2$ concentration to be ramped (e.g., linearly or non-linearly increased or decreased). For example, the concentration of $CO_2$ may be ramped from a starting value of 0 $\mu$mol mol$^{-1}$ or a higher value to about 1000 $\mu$mol mol$^{-1}$ or a lesser or greater value, or the $CO_2$ concentration may be ramped from a starting value of about 1000 $\mu$mol mol$^{-1}$ or a greater or lesser value down to 0 $\mu$mol mol$^{-1}$ or down to an intermediate value. The rate of attenuation or increase may be controlled as desired, e.g., between 1 µmol mol$^{-1}$ min$^{-1}$ and 2000 µmol mol$^{-1}$ min$^{-1}$. The ramping may be linear, e.g., continuous and linear, or the ramping may take on a non-linear curved shape. In an embodiment, there are no "pauses" in the $CO_2$ ramping. In other embodiments, pauses are included into the ramping.

Figure 2:
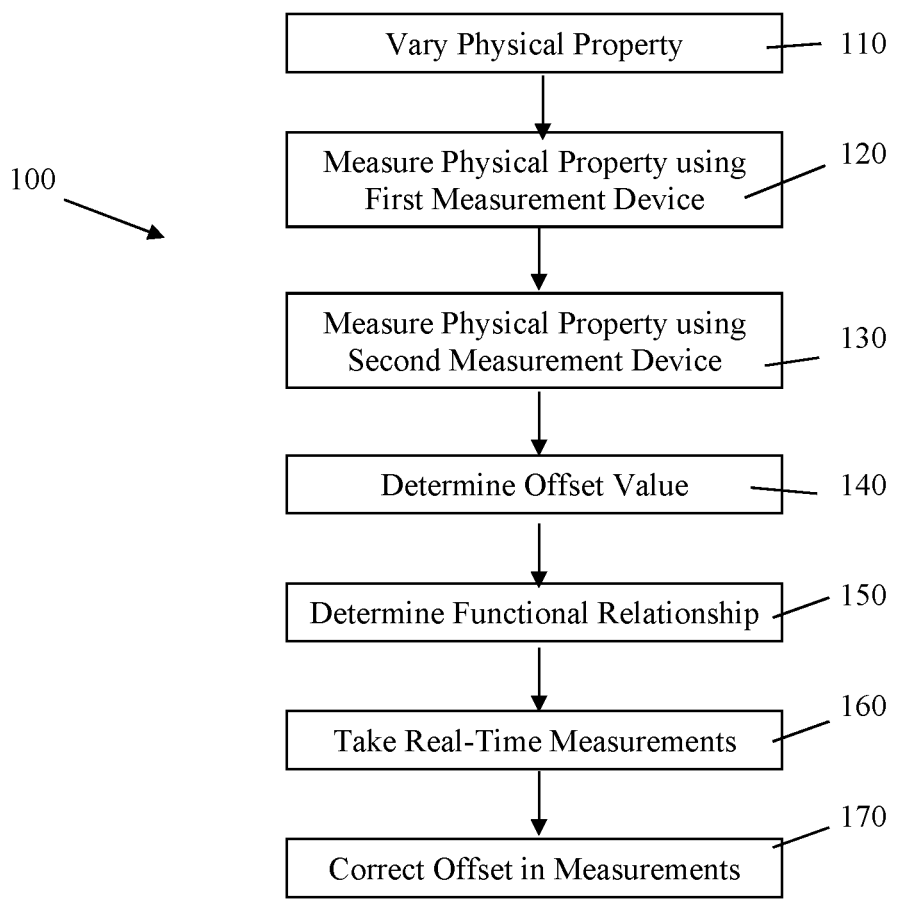
FIG. 2 illustrates a method 100 of determining and correcting for offset in a differential measurement system according to one embodiment.

FIG. 2 illustrates a method 100 of determining and correcting for offset in a differential measurement system according to one embodiment. In step 110, a physical property value (e.g., concentration of $CO_2$ introduced into a gas flow line) is provided to a first measurement device and a second measurement device, and that property is varied over time. In step 120, the physical property is measured using the first measurement device to determine a first measurement value. In step 130, the physical property is measured using the second measurement device to determine a second measurement value. Steps 110, 120 and 130 may be repeated one or multiple times to build up a data set of measured values for each of a plurality of different property values (e.g., different $CO_2$ concentration values). In step 140, offset values between corresponding first and second measurement values are determined. In step 150, a functional relationship between the offset values and measurements of the first measurement device (or second measurement device) is determined. Step 150 may include applying a fit function to the offset values. In step 160, real-time differential measurements of the physical property are taken (e.g., in a gas exchange analysis system, measurements with a controlled $CO_2$ flow and with a leaf or other photosynthesis capable substance in the sample chamber 30 may be taken by the two gas analyzers 40, 50). In step 170, corrections are made to the real-time differential measurements based on the determined functional relationship.

In certain embodiments, the control system or other intelligence module, which may include a processing component or components such as one or more processors and associated memory and/or storage, is configured to control, and to receive and process data from, the measurement devices to implement the methods disclosed herein, e.g., perform the offset calculations and correct real-time measurements.

Each processor or processing component is configured to implement functionality and/or process instructions for execution, for example, instructions stored in memory or instructions stored on storage devices, and may be implemented as an ASIC including an integrated instruction set. A memory, which may be a non-transient computer-readable storage medium, is configured to store information during operation. In some embodiments, a memory includes a temporary memory, area for information not to be maintained when the processing component is turned OFF. Examples of such temporary memory include volatile memories such as random access memories (RAM), dynamic random access memories (DRAM), and static random access memories (SRAM). The memory maintains program instructions for execution by the processing component.

Storage devices also include one or more non-transient computer-readable storage media. Storage devices are generally configured to store larger amounts of information than the memory. Storage devices may further be configured for long-term storage of information. In some examples, storage devices include non-volatile storage elements. Non-limiting examples of non-volatile storage elements include magnetic hard disks, optical discs, floppy discs, flash memories, or forms of electrically programmable memories (EPROM) or electrically erasable and programmable (EEPROM) memories.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. For example, the methodologies disclosed herein may be useful to determine response to other gases, or components in a gas, such as $H_2O$, $O_2$, etc. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method for determining real-time offset corrections in a gas analysis system having a first gas analyzer and a second gas analyzer, the method comprising:
   supplying a varying concentration of gas over a range of gas concentrations to the first gas analyzer through a first gas flow line and to the second gas analyzer through a second gas flow line;
   for each of a plurality of different supplied gas concentrations within the range of gas concentrations:
   a) measuring a first gas concentration value using the first gas analyzer;
   b) measuring a second gas concentration value using the second gas analyzer; and c) determining an offset value between each corresponding first and second gas concentration value;

determining a functional relationship between the plurality of offset values and the measured gas concentration values of the first gas analyzer; and thereafter taking real-time gas concentration measurement values and dynamically adjusting the real-time gas concentration measurement values of the first gas analyzer based on the functional relationship.

2. The method of claim 1, wherein the gas analysis system further includes an enclosed sample chamber defining a measurement volume for analysis of a photosynthesis capable sample, the sample chamber having an inlet port coupled with the first gas flow line and an outlet port coupled with an inlet port of the first gas analyzer, wherein the taking real-time gas concentration measurements and dynamically adjusting the real-time gas concentration measurement values of the first gas analyzer based on the functional relationship includes:

with a photosynthesis capable sample in the sample chamber, taking real-time gas concentration measurement values using a supplied gas concentration within the range of gas concentrations and adjusting the real-time gas concentration measurement values of the first gas analyzer based on the determined functional relationship.

3. The method of claim 2, wherein the photosynthesis capable sample includes a leaf.

4. The method of claim 1, wherein the supplying includes continuously varying the concentration of the gas from a first concentration to a second concentration over a measurement time period, and wherein the measuring a first gas concentration value using the first gas analyzer and the measuring a second gas concentration value using the second gas analyzer occur simultaneously during the measurement time period.

5. The method of claim 1, wherein the gas includes $CO_2$, and wherein the supplying a varying concentration of gas includes only increasing the concentration of $CO_2$, or only decreasing the concentration of $CO_2$, or varying the concentration of $CO_2$ from a first value to a second value and then varying the concentration of $CO_2$ from the second value to the first value.

6. The method of claim 1, wherein the determining a functional relationship includes applying a fit function to the plurality of offset values.

7. The method of claim 1, wherein the determining a functional relationship includes segmenting the plurality of offset values into two or more range segments, each range segment corresponding to a portion of the range of gas concentrations, and for each range segment applying a separate segment fit function to the offset values in that range segment.

8. The method of claim 1, wherein the measuring of the first and second gas concentration values occurs when the concentration of gas supplied to the first gas analyzer and to the second gas analyzer reaches a steady state.

9. The method of claim 1, wherein the supplying includes varying the concentration of the gas from a first concentration to a second concentration in a stepwise manner.

10. A gas analysis system, the system comprising:

a gas source coupled to a first gas flow line and a second gas flow line, the gas source configured to supply a varying concentration of gas over a range of gas concentrations to the first gas flow line and the second gas flow line;

a first gas analyzer coupled to the first gas flow line and configured to measure a first concentration of the gas received from the first gas flow line;

a second gas analyzer coupled to the second gas flow line and configured to measure a second concentration of the gas received from the second gas flow line; and a control circuit, the control circuit configured to:

send a control signal to the gas source to control the gas source to adjust the concentration of a gas supplied to the first and second gas flow lines; and for each of a plurality of different supplied gas concentrations within the range of gas concentrations:

receive a first gas concentration measurement value from the first gas analyzer; and receive a second gas concentration measurement value from the second gas analyzer;

the control circuit further being configured to:

determine a plurality of offset values between the plurality of corresponding first and second gas concentration measurement values;

determine a functional relationship between the plurality of offset values and the gas concentration measurement values of the first gas analyzer; and thereafter control the system to take real-time gas concentration measurement values and dynamically adjust the real-time gas concentration measurement values of the first gas analyzer based on the functional relationship.

11. The system of claim 10, wherein the gas analysis system further includes an enclosed sample chamber defining a measurement volume for analysis of a photosynthesis capable sample, the sample chamber having an inlet port coupled with the first gas flow line and an outlet port coupled with an inlet port of the first gas analyzer, wherein the real-time gas concentration measurement values are taken with a photosynthesis capable sample in the sample chamber.

12. The system of claim 11, wherein the photosynthesis capable sample includes a leaf.

13. The system of claim 10, wherein the gas source is configured to supply a continuously varying concentration of the gas from a first concentration to a second concentration over a measurement time period.

14. The system of claim 10, wherein the gas includes $CO_2$, and wherein the gas source is configured to supply the varying concentration of gas by only increasing the concentration of $CO_2$, or only decreasing the concentration of $CO_2$, or varying the concentration of $CO_2$ from a first value to a second value and then varying the concentration of $CO_2$ from the second value to the first value.

15. The system of claim 10, wherein the control circuit is further configured to determine the functional relationship by applying a fit function to the plurality of offset values.

16. The system of claim 10, wherein the gas source is configured to supply the varying concentration of the gas from a first concentration to a second concentration in a stepwise manner.

17. The system of claim 10, wherein the control circuit is further configured to determine the functional relationship by segmenting the plurality of offset values into two or more range segments, each range segment corresponding to a portion of the range of gas concentrations, and for each range segment applying a separate segment fit function to the offset values in that range segment.

18. A method for determining real-time offset corrections in a differential measurement system having a first measurement device and a second measurement device, the method comprising:
for each of a plurality of different supplied property values of a physical property within a range of property values:
  a) obtaining a first measurement value of the physical property using the first measurement device; and
  b) obtaining a second measurement value of the physical property using the second measurement device;
determining a plurality of offset values between the plurality of corresponding first and second physical property measurement values; and
determining a functional relationship between the plurality of offset values and the physical property measurement values of the first measurement device.

19. The method of claim 18, further including taking real-time physical property measurement values and adjusting the real-time physical property measurement values of the first measurement device based on the functional relationship or adjusting the real-time physical property measurement values of the second measurement device based on the functional relationship or adjusting a difference between the real-time physical property measurement values of the first measurement device and the second measurement device based on the functional relationship.

20. A differential measurement system, the system comprising:
a first measurement device configured to measure a physical property;
a second measurement device configured to measure the physical property; and
a control circuit, the control circuit configured to:
for each of a plurality of different supplied property values of the physical property within a range of property values:
  receive a first measurement value of the physical property from the first measurement device; and
  receive a second measurement value of the physical property from the second measurement device;
the control circuit further being configured to:
determine a plurality of offset values between the plurality of corresponding first and second physical property measurement values; and
determine a functional relationship between the plurality of offset values and the physical property measurement values of the first measurement device.

21. The system of claim 20, wherein the control circuit is further configured to control the system to take real-time physical property measurement values and adjust the real-time physical property measurement values of the first measurement device based on the functional relationship.

* * * * *